United States Patent [19]
Carola

[11] Patent Number: 5,474,112
[45] Date of Patent: Dec. 12, 1995

[54] DEVICE FOR PREVENTING "GAS-LOCK" DURING THE TRANSFER OF A LIQUID IN A CLOSED SYSTEM, AN ARRANGEMENT CONTAINING THE SAME AND A METHOD OF USE

[75] Inventor: Armand Carola, Montréal, Canada

[73] Assignee: Technimeca Ltd., Montee de Liesse St-Laurent, Canada

[21] Appl. No.: 229,001

[22] Filed: Apr. 18, 1994

[30] Foreign Application Priority Data

Dec. 7, 1993 [CA] Canada ................................. 2110851

[51] Int. Cl.⁶ ........................... B65B 31/00; B67C 3/00
[52] U.S. Cl. .................. 141/7; 141/18; 141/290; 141/306; 141/366; 137/587; 137/43; 222/500
[58] Field of Search ................. 141/7, 45, 59, 141/290, 301, 303, 304, 306, 307, 308, 319, 320, 325, 326, 364, 366, 367, 375, 386, 18, 273, 21, 274; 222/500, 481, 481.5; 137/587, 43, 590, 592; 128/204.17, 911, 912, 200.14, 200.16, 200.19; 261/72.1, DIG. 65

[56] References Cited

U.S. PATENT DOCUMENTS

| | | | |
|---|---|---|---|
| 1,984,005 | 12/1934 | Young | 221/28 |
| 2,168,050 | 8/1939 | Slipikas | 222/500 |
| 2,261,037 | 10/1941 | Schwab | 137/587 |
| 2,501,511 | 3/1950 | Grosbois | 226/111 |
| 2,991,897 | 7/1961 | Burnett | 215/21 |
| 3,233,797 | 2/1966 | Conry | 222/500 |
| 3,450,171 | 6/1969 | Takiguchi | 141/20 |
| 3,536,107 | 1/1970 | Schreiber et al. | 141/18 |
| 3,536,108 | 1/1968 | Schreiber | 141/18 |
| 4,531,659 | 7/1985 | Wright | 222/190 |
| 4,705,195 | 11/1987 | Heck | 222/207 |
| 4,867,212 | 9/1989 | Mohr et al. | 141/290 |
| 4,978,038 | 12/1990 | Sullivan | 137/43 |
| 5,144,991 | 9/1992 | Wallroth et al. | 141/192 |
| 5,170,823 | 12/1992 | Gregory et al. | 141/382 |
| 5,181,497 | 1/1993 | Matsushita et al. | 123/520 |

FOREIGN PATENT DOCUMENTS 0242979  3/1987  European Pat. Off. .

Primary Examiner—Henry J. Recla
Assistant Examiner—Steven O. Douglas
Attorney, Agent, or Firm—Willian Brinks Hofer Gilson & Lione

[57] ABSTRACT

A device for preventing a "gas-lock" comprising a hollow casing defining a reservoir of given capacity and having a lower portion and a set of three openings, that is a first and a third openings substantially positioned at the lower portion of the casing and a second opening positioned near a bottom of the reservoir; a second connection for connecting a corresponding end of the second channel with the second opening; a third channel having opposite ends, one end being positioned near a portion of the first container that is opposite to the aperture of the first container; a third connection for connecting the opposite end of the third channel with the first opening; a check valve; a fourth connection for connecting the check valve with respect to the third opening and for selectively, enabling the liquid contained in the first container to pass through the third opening; the capacity of the reservoir being sufficient to collect when the first container is turned upside-down to have its third channel above the reservoir, all the liquid that may fill this third channel and allow inside the reservoir a free passage for the gas between the first and second openings. Also relates to an arrangement containing the device and a method use.

24 Claims, 5 Drawing Sheets

DEVICE FOR PREVENTING "GAS-LOCK" DURING THE TRANSFER OF A LIQUID IN A CLOSED SYSTEM, AN ARRANGEMENT CONTAINING THE SAME AND A METHOD OF USE

FIELD OF THE INVENTION

The present invention relates to a device for preventing a "gas-lock" when a liquid is transferred by gravity from a first container to a second container and vice versa, each container having one aperture through which a fluid matter may flow. These apertures are connected together by first connecting means, to make the containers and first connecting means defining a closed system filled with at least one liquid and at least one gas. The invention also relates to an arrangement comprising the aforesaid device and to a method using the aforesaid device.

BACKGROUND OF THE INVENTION

For diverse purposes, it is desirable to transfer a liquid from a container to an other in a closed system, especially for filling and/or emptying an anesthetic vaporizer with an anesthetic in the liquid form. Indeed, it is important for the protection of the staff, to avoid the diffusion of the anesthetic in the working area.

For example, U.S. Pat. No. 5,144,991 describes an arrangement for filling and emptying an anesthetic vaporizer with an anesthetic liquid from a supply vessel by means of a filling channel. The filling arrangement includes a venting channel and a connecting piece adapted to fit on an anesthetic vaporizer and has a blocking device which is mounted in the channel assembly of the filling channel and venting channel.

U.S. Pat. No. 3,536,107 discloses a container provided with air vent means having gravity actuated means controlling the air vent means when the container is upright or inverted. The use of a ball, moving in a housing and with respect to a ball seat, by reason of gravity, to obturate or liberate openings, is disclosed in U.S. Pat. No. 4,531,659 and U.S. Pat. No. 2,991,897.

It is well known in the art that when an open neck container containing a liquid is turned upside-down, the flow of liquid may be impeded by a vacuum created in the container. This phenomena is called "gas-lock", especially "air-lock". An example of such an "air-lock" was noted when a volume of air is trapped by a liquid in the bottom of the first container and prevent it to flow in the venting channel after the container was turned upside-down.

U.S. Pat. No. 4,705,195 discloses a liquid dispenser which includes a pump chamber, connected to a storage chamber, and a valve body extending through the passage and controlling the liquid flow. This device is not adapted to a closed system, considering that it has no separating channels for the liquid and the gas.

Therefore, there is a very strong need for a device and a method allowing to transfer a liquid in a closed system without having the problems noted with devices of the prior art.

SUMMARY OF THE INVENTION

A first object of the present invention is to provide a device allowing in a closed system, to continuously and simultaneously replace the liquid transferred from one container to another by the gas contained in the other of said containers (i.e. the container where the liquid is transferred).

Another object of the present invention is to provide a device that can be adapted to existing containers, especially bottles used for the filling and/or emptying of anesthetic vaporizers.

Another object of the present invention is to provide a device that is cheap and easy to manufacture, reliable and very easy to install in existing containers, especially bottles for the filling and/or emptying of anesthetic vaporizers.

The invention also relates to a device that is reusable and/or transferable from one container to another since it may optionally define a part of the first connecting means.

The invention also relates to an arrangement comprising the aforesaid device and said first connecting means.

The invention also relates to a method that is distinct over methods actually known, since it al lows to prevent the presence of a "gas-lock" when a liquid is transferred by gravity from a first container to a second container and vice versa, in a closed system.

SUMMARY OF THE INVENTION

More particularly, the present invention relates to a device for preventing a "gas-lock" when a liquid is transferred by gravity from a first container to a second container and vice versa, each of the containers having at least one aperture through which fluid matters may flow, these apertures being connectable together by first connecting means provided with channels, said containers and channels when connected, defining a closed system filled with at least one liquid and at least one gas, a first of said channels defining essentially a transfer channel for the liquid and a second of said channels defining essentially a venting channel for the gas, each of said channels having opposite ends with one end thereof substantially positioned near a portion of the first container that is substantially close of the aperture of the first container, wherein said device comprises:

a hollow casing defining a reservoir of given capacity and having a lower portion and a set of three openings, said openings consisting of:
  a first opening substantially positioned at the lower portion of the hollow casing;
  a second opening positioned near a bottom of the reservoir;
  a third opening substantially positioned at a lower portion of the casing;
 second connecting means for connecting a corresponding end of the second channel to said second opening;
 a third channel having opposite ends, one end of said third channel being positioned near a portion of the first container that is opposite to its aperture;
 third connecting means for connecting the end of the third channel that is opposite the one positioned near a portion of the first container that is opposite the aperture of the first container, to the first opening;
 a gravity actuated means for selectively preventing or allowing the liquid contained in the first container to pass through the third opening (preferably a gravity actuated check valve and a fourth connecting means for connecting said check valve with respect to the third opening and for selectively preventing or allowing the liquid contained in the first container to pass through said third opening);
 the capacity of the reservoir being sufficient to collect when the third channel is positioned above it, all the liquid that may be contained in the third channel and allow inside the hollow casing a free passage for the gas between said first and second openings.

The invention also relates to an arrangement of the type comprising the aforesaid device in association with a first container and first connecting means adapted to put the first container in fluid communication with a second container, each of the containers having at least one aperture through which fluid matters may flow, these apertures being to be connected together by said first connecting means which is provided with channels, said containers and channels when connected, being intended to define a closed system filled with at least one liquid and at least one gas, a first of said channels defining essentially a transfer channel for the liquid and a second of said channels defining essentially a venting channel for the gas, each of said channels having opposite ends with one end thereof substantially positioned near a portion of the first container that is substantially close of the aperture of the first container.

Advantageously, the second opening may be part of a tube having opposite ends and being housed at least in part, inside the hollow casing, one end of this tube being positioned near the bottom of the hollow casing while the opposite end is preferably positioned outside the reservoir and connected with a corresponding end of the venting channel. Preferably, the end of the tube that is housed in the reservoir is closed, and at least one orifice, for example two orifices, are provided in the longitudinal wall of said tube, in the vicinity of said end near the bottom of the reservoir.

Advantageously, the gravity actuated check valve (hereinafter named check valve) may comprise:

- a sleeve having opposite ends and at least one lateral opening;
- means for connecting one end of said sleeve to the hollow casing and aligning it with the third opening;
- a member, advantageously a sphere and more preferably a ball such as a steel ball, housed inside said sleeve;
- a seat for said member, said seat having advantageously a shape adapted to match with the one of the member and being preferably positioned between the third opening of the hollow casing and the lateral opening of the sleeve;
- retaining means for retaining the member inside the sleeve;

said member being movable by gravity between two distinct positions, that is a first position where it is seated against the seat to substantially seal the third opening, and a second position where it contacts the retaining means and allows a fluid communication between the lateral opening of the sleeve and the inside of the hollow casing through said third opening.

Advantageously, the second container is part of an anesthetic vaporizer provided with two apertures, said apertures respectively defining a filling or emptying socket and each comprising two pairs of channels communicating with said second container. The pair of channels of the filling socket respectively defining when filling of the second container, transfer and venting channels. The pair of channels of the emptying socket respectively defining when emptying the second container, transfer and venting channels.

Alternatively, both sockets may be replaced by only one socket provided with two pairs of channels.

Advantageously, the first container may consist of a bottle having a neck and an open top defining the aperture of said bottle.

Advantageously, first means for connecting apertures of the first and second containers together comprise:

- a key having opposite ends and an outer longitudinal surface, preferably an outer longitudinal cylindrical surface, said key being provided with a transfer channel and a venting channel having opposite ends, one end of each channel being provided in one end of the key while the opposite end is provided in the outer longitudinal surface of said key;
- a rigid curved tube having opposite ends;
- fifth connecting means for connecting, preferably pivotally connecting, one end of said rigid curved tube on one end of the key and, directly or indirectly, with the transfer channel of the key, and sixth connecting means for connecting the opposite end of said rigid curved tube and set the aperture of the first container in fluid communication with the rigid curved tube;
- a venting tube having opposite ends and defining a venting channel;
- seventh connecting means for connecting one end of said venting tube on the venting channel of the key, and eighth connecting means for connecting the opposite end of the venting tube to the second opening of the hollow casing;

one of ends of the transfer and venting channels of the key being positioned on the outer longitudinal surface of said key to be aligned with corresponding transfer and venting channels, for filling or emptying of the second container by mere rotation of the key in the aperture around a longitudinal axis of the key.

Tha aforesaid fifth to seventh connecting means advantageously correspond to a preferred definition of the above mentionned first connecting means. More particularly, the eighth connecting means may correspond to a particularly preferred definition of the second connecting means.

Advantageously, the venting tube may be co-axially positioned inside the rigid curved tube.

Advantageously, the gas may consist of air eventually in admixture with other gas.

More particularly, the invention also relates to a method for the transfer by gravity of a liquid from a first container to a second container and vice versa while preventing a "gas-lock", each container having at least one aperture through which fluids matters may flow, these apertures being connectable together by first connecting means provided with channels, said containers and channels when connected, defining a closed system filled with at least one liquid and at least one gas, a first of said channels defining essentially a transfer channel for the liquid and a second of said channels defining essentially a venting channel for the gas, each of said channels having opposite ends with one end thereof substantially positioned near a portion of the first container that is close of the aperture of the first container, the end of the venting channel being provided with a device comprising:

- a hollow casing defining a reservoir of given capacity and having a lower portion and a set of three openings, said openings consisting of:
  - a first opening substantially positioned at the lower portion of the hollow casing;
  - a second opening positioned near a bottom of the reservoir;
  - a third opening substantially positioned at a lower portion of the casing;
- second connecting means for connecting a corresponding end of the second channel to said second opening;

a third channel having opposite ends, one end of said third channel being positioned near a portion of the first container that is opposite to the aperture of the first container;

third connecting means for connecting the end of the third channel that is opposite the one positioned near a portion of the first container that is opposite the aperture of the first container, to the first opening;

a gravity actuated means for selectively preventing or allowing the liquid contained in the first container to pass through the third opening (preferably a gravity actuated check valve and a fourth means for connecting said check valve with respect to the third opening and for selectively preventing or allowing the liquid contained in the first container to pass through said third opening);

the capacity of the reservoir being sufficient to collect when the third channel is positioned above the reservoir, all the liquid that may be contained in the third channel and allow inside the hollow casing a free passage for gas between said first and second openings.

According to the aforesaid method, when the first and the second containers are connected by first connecting means for filling purpose and said first container contains a liquid to be transferred in the second container, the first container is moved (preferably by pivoting of the key inside the aperture of the second container or more preferably by pivoting of the end of the rigid curved tube on a corresponding end of the key) from a position located at a point lower than the second conainer to a position located at a point higher than the second container to pass the liquid through the aperture of the first container, the transfer channel and the aperture of the second container to fill this second container while the liquid eventually contained in the third channel is transferred in the reservoir of the device and the gas contained in the second container is vented from the second container and transferred in the first reservoir through the aperture of the second container, the venting channel and the aperture of the first container, the second opening of the device, the hollow casing, the first opening of the device and the third channel.

According to the aforesaid method, when the first and the second container are connected by first connecting means for emptying purposes and said second container contains a liquid to be transferred in the first container, the first container is moved (preferably by pivoting of the key inside the aperture of the second container or more preferably by pivoting of the end of the rigid curved tube on a corresponding end of the key) from a position located at a point higher than the second container to a position located at a point lower than the second container to make the liquid to pass through the aperture of the second container, the transfer channel, the aperture of the first container while the gas contained in the first container is vented from the first container and transferred in the second container through the aperture of the first container via the check valve, the third opening of the hollow casing, the hollow casing, the second opening of the hollow casing, the venting channel and the aperture of the second channel.

BRIEF DESCRIPTION OF THE DRAWINGS

The present invention will be better understood with reference to the following description of preferred embodiment thereof, with reference to the following drawings.

Figure 1:
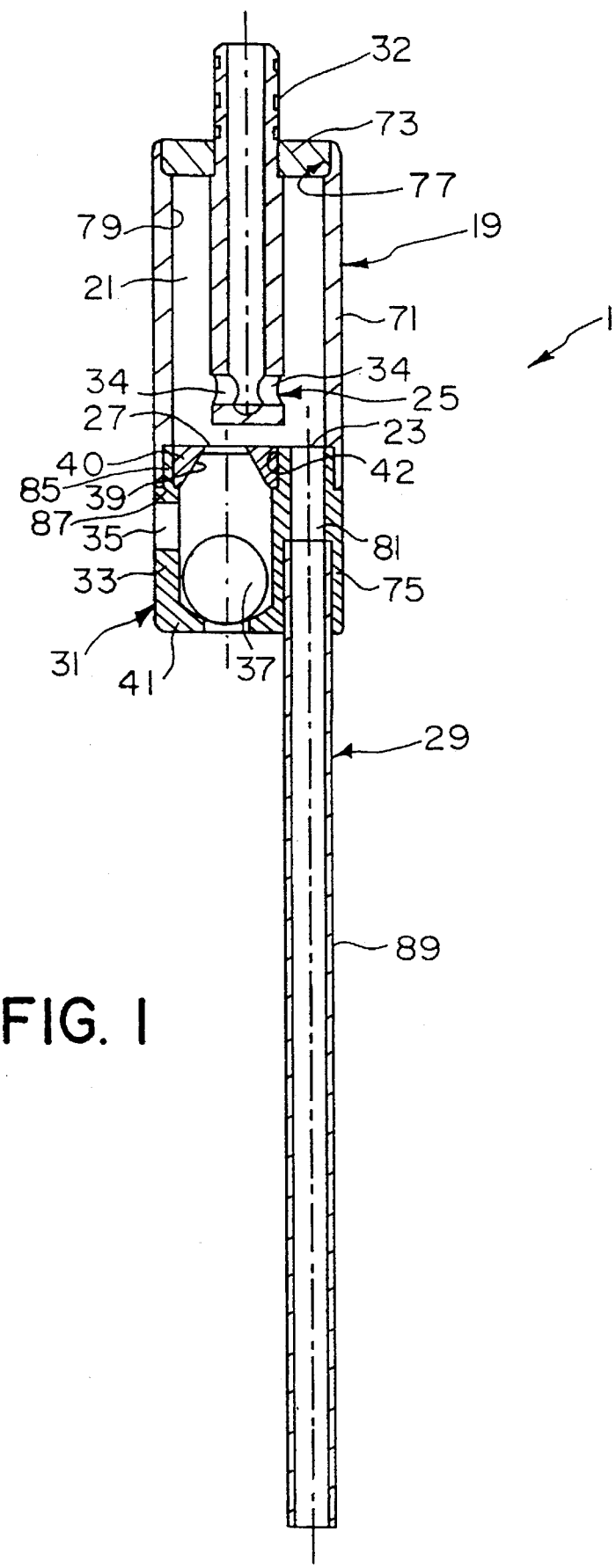
FIG. 1: is a cross-sectional view of a preferred embodiment of a device according to the invention in an opened position.
Figure 2:
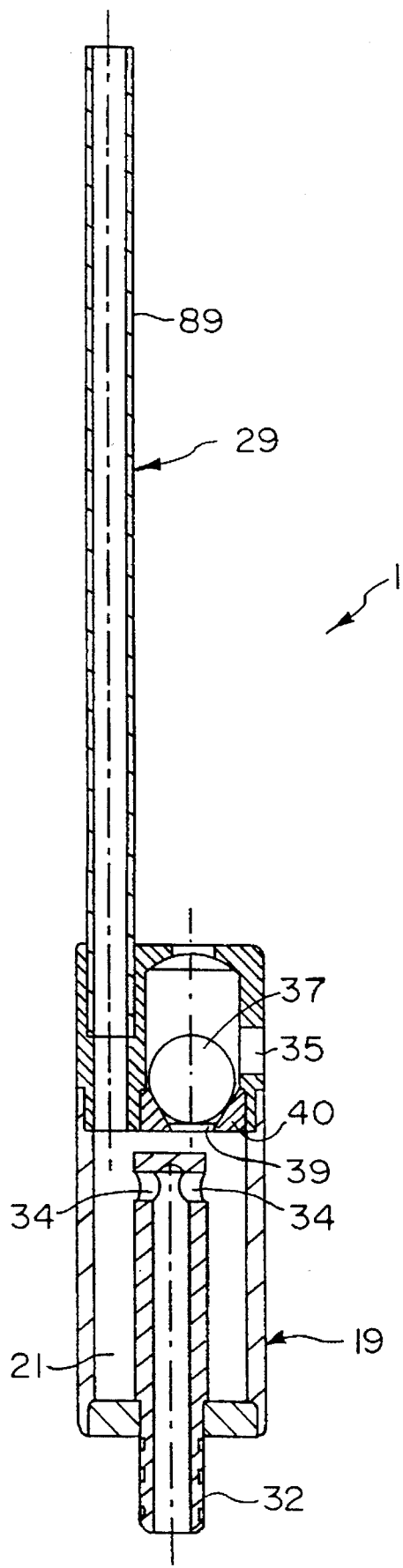
FIG. 2: is a cross-sectional view of a preferred embodiment of a device according to the invention in closed position.

DESCRIPTION OF PREFERRED EMBODIMENTS OF THE INVENTION:

FIGS. 1 and 2 represents a preferred embodiment of a device 1 according to the invention. More particularly, this device 1 prevents a "gas-lock" when a liquid is transferred by gravity from a first container, especially a bottle 3, to a second container, especially the reservoir 5 of an anesthetic vaporizer 7, and vice versa. Each of the containers has one aperture through which fluid matters may flow. Especially, the bottle 3 has a neck 9 and an aperture 11, and the reservoir of the anesthetic vaporizer 7 has an aperture 13. Because anesthetic vaporisers are devices well known in the art, it will be not described in detail. Of course, means are provided to seal the reservoir 5 when the key 43 is not inserted in a socket 14a or 14b. The apertures 11 and 13 are connectable together by first connecting means provided with channels, said containers and channels when connected, defining a closed system filled with at least one liquid and at least one gas. A first of said channels is essentially a transfer channel 15 for the liquid and a second of said channels is essentially a venting channel 17 for the gas. Each of said channels 15 and 17 have opposite ends with one end thereof substantially positioned near a portion of the neck 9 of the bottle 3, especially substantially close of the aperture 11.

The device of FIGS. 1 and 2, comprises:

a hollow casing 19 defining a reservoir 21 of given capacity and having a lower portion and a set of three openings, said openings consisting of:

a first opening 23 substantially positioned at the lower portion of the hollow casing 19;

a second opening 25 positioned near a bottom of the reservoir 21;

a third opening 27 substantially positioned at a lower portion of the hollow casing 19;

second connecting means for connecting a corresponding end of the venting channel 17 to the second opening 25;

a third channel 29 having opposite ends, one end of said third channel 29 being positioned near a portion of the bottle 3 that is opposite to its aperture 11;

third connecting means for connecting the end of the third channel 29 that is opposite the one positioned near a portion of the bottle 3 that is opposite to its aperture 11;

a gravity actuated check valve 31;

fourth connecting means for connecting the check valve 31 with respect to the third opening 27 and for selectively preventing or allowing the liquid contained in the bottle 3 to pass through said third opening 27;

the capacity of the reservoir 21 being sufficient to collect when the third channel 29 is positioned above the reservoir 21, all the liquid that may be contained in the third channel 29 and allow inside the hollow casing 19 a free passage for gas between said first opening 23 and second opening 25.

According to a particularly preferred embodiment of the invention, the second opening 25 may be part of a tube 32 having opposite ends and being at least housed inside the hollow casing 19, one end of this tube 32 being positioned near the bottom of the hollow casing 19 while the opposite end is connected with the corresponding end of the venting channel 17.

According to a particularly preferred embodiment of the invention, the check valve 31 may comprise:

a sleeve 33 having opposite ends and at least one lateral opening 35;

means for connecting one end of said sleeve 35 to the third opening 27;

a member, especially a sphere and more particularly a ball such as a steel ball 37, housed inside said sleeve 33;

a seat 39 for the member (e.g. a steel ball 37), said seat 39 being positioned between the third opening 27 and the lateral opening 35 of the sleeve 33;

retaining means such as the element 41 for retaining the member (e.g. the steel ball 37) inside the sleeve 33;

said member (e.g. the steel ball 37) being movable by gravity between two distinct positions, that is a first position where it is seated against the seat 39 to substantially seal the third opening 27, and a second position where it contacts said retaining means, especially the element 41, and allow a fluid communication between the lateral opening 35 of the sleeve 33 and the inside of the hollow casing 19 through said third opening 27.

The hollow casing 19 preferably comprises a sleeve 71, a washer 73, the tube 32 and a member 75. The tube 32 is mounted in an opening provided in the washer 73. Preferably, the tube 32 may be fastened in said opening by any appropriate means such as gluing, welding, ect. However, the tube 32 may be merely inserted tightly in said opening, the friction existing between the opening of the washer 73 and the outer surface of the tube being sufficient to hold this latter firmly in place.

Advantageously, the washer 73 may be mounted on one end of the sleeve 71 by any appropriate means such as gluing, welding, ect. Preferably, the washer 73 may be merely press fitted in a groove 77 provided in the inner surface 79 of the sleeve 71 at one end of said sleeve 71.

Advantageously, the end of the tube 32 that is positioned outside the hollow casing 19 defines with the end of the venting tube 49, said second connecting means. More particularly, the venting tube 49 is forced over the tube 32. The friction existing between both tubes 32 and 49 is sufficient to keep them together.

Advantageously, the member 75 consists of a plug comprising the sleeve 33, the lateral opening 35, the steel ball 37, the seat 39 and the element 41, and comprising a fourth channel 81. This member 75 may be fastened to the remaining end of the sleeve 33 by all appropriate means such as gluing, welding, ect. Preferably, the member 75 and the remaining end of the sleeve 71 are both provided with a groove 85 and 87 that may be press fitted one against the other. The friction existing between both grooves is sufficient to keep them together. Preferably, one end of the sleeve 33 in the member 75 defines the third opening 27. Preferably, the fourth channel 81 may defines the first opening 23.

Advantageously, the third channel 29 may consist of a tube 89 that is forced in the fourth channel 81. The fourth channel 81 may be optionally provided with a receiving groove for one end of the tube 89. The third connecting means for connecting the third channel 29 to the first opening are preferably represented when the tube 89 is forced in a receiving groove provided in the fourth channel 81.

The capacity of the reservoir 21 is preferably such to keep clear a volume of said hollow casing 19 comprises between the part of the tube 32 where orifices 34 appears and the first opening 23. This capacity of the reservoir 5 is preferably equal or superior to the inner volume of the third channel 29.

Advantageously, the seat 39 is defined on the underneath of a washer 40 that is mounted on one end of the sleeve 33. Advantageously, the inner surface of the sleeve 33 is provided with a groove 42 where the steel ball 37 may be introduced in the sleeve 33 by forcing it therein. The steel ball 37 may consist of a carbon chromium ball. An externally surface finish may be executed on the steel ball by plating with it with nickel and for example nickel MIL-C-26074. calls 4, grade 3. More particularly, washer 42 is fastened in the groove 42 by any appropriate means such as for example gluing, welding, ect. Preferably, the washer 40 is merely press fitted in the groove 42. The friction between the washer 40 and the groove 42 is sufficient to keep them together.

The device according to the invention may be advantageously adapted on a device for the filling and the emptying of vaporizers with anesthetic agent. These operations must be done in a closed circuit (leak-proof) to insure that no agent or vapour leaks to pollute the atmosphere of working area.

Figure 3:
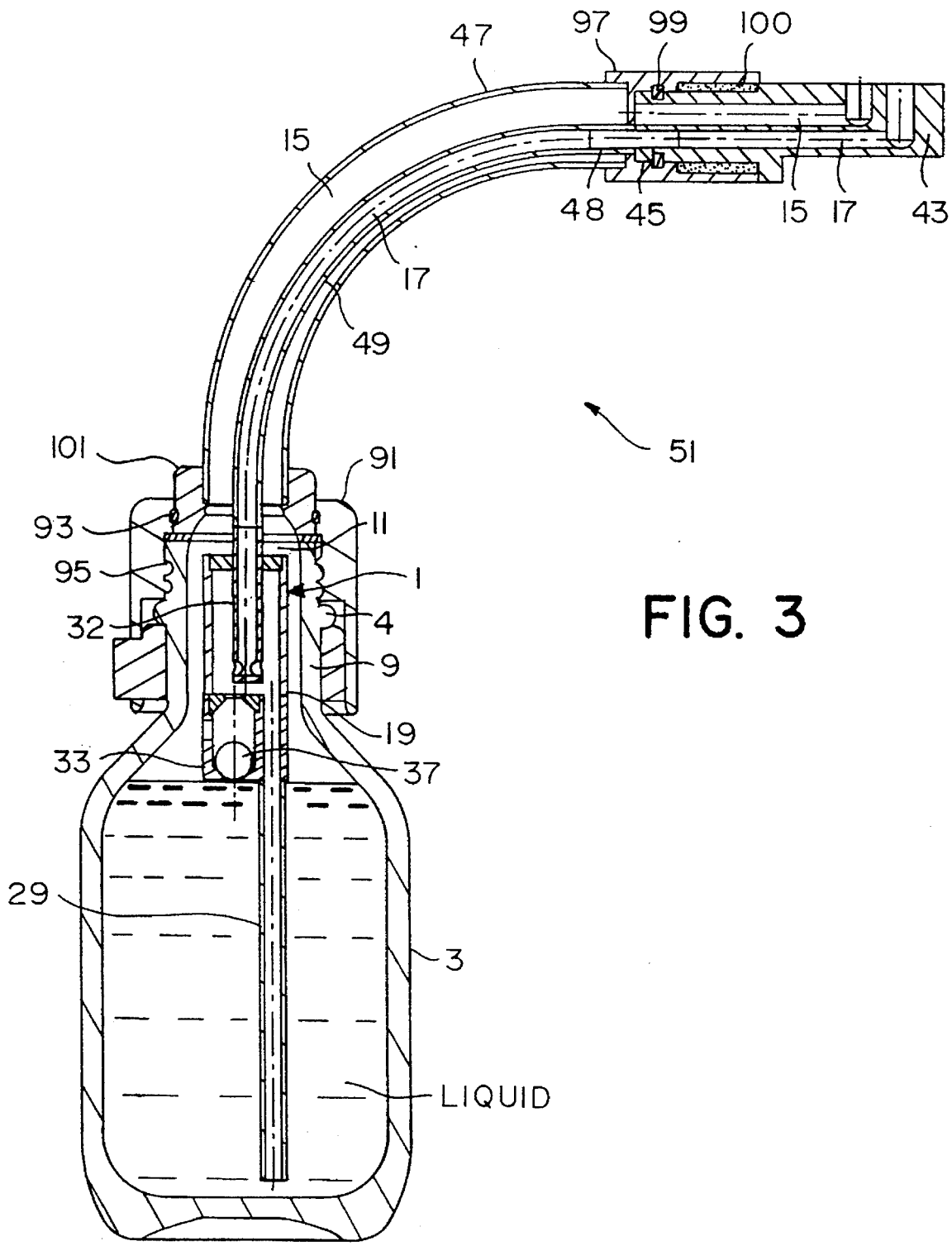
FIG. 3: is a cross-sectional view of an arrangement comprising a device according to the invention for supplying and withdrawing liquid in a closed circuit, the check valve of the device being in a position as in FIG. 1.

FIG. 3 of the drawing shows an arrangement according to the invention in an emptying position. It comprises a bottle 3, a reservoir 5 of an anesthetic vaporizer 7, a rigid curved tube 47, with a screw cap 91 on the bottle side, and a key preferably an indexed key) 43 which corresponds to the filling and emptying apertures 13 of the reservoir 5 of the anesthetic vaporizer 7.

It is to be noted that the key 43 corresponds to an indexing system in general use worldwide to eliminate all risks of cross-filling or cross-contamination of anesthetic agents during the utilization of the vaporizer. Therefore, there is no need to explain in detail this key 43 and the aperture 13 of the anesthetic vaporizer 7.

The indexed key 43 may consist of an inlet adapter for liquid air, and may be optionnaly fastened to the rigid curved tube 47 by a retaining snap ring 99 and a teflon spacer ring 100 is preferably provided on said key to secure imperviousness.

The rigid curved tube 47 may be optionally provided with a inner venting tube 49. On the key side of the rigid curved tube 47, the tube 49 is provided with an air or gas tube connector whereas rigid curved tube 47 is provided, especially by the mean of a silver soldering, with a swivel seal bushing 97 having retaining snap ring 99 to be fastened to the key 43. On the bottle side the rigid curved tube 47 is provided with an adapter-bottle cap 101 and fastened with a silver soldering. The tube 49 may be connected with the external end of the tube 32.

A surface finish can be executed on the rigid curved tube 47, the swivel seal bushing 97 and the adapter bottle cap 101 by plating with nickel and, for example MIL-C-26074 class 4, grade B nickel.

The key 43 and the rigid curved tube 47 are connected together by press fitting the connector 48 in said key, then by installing retaining snap ring 93 on said key 43 and then by pushing the venting tube 49 on the air tube connector 48.

The first container, which can advantageously be a bottle 3 advantageously made of isoflurane, may have a neck 9 which may be provided with a plastic security collar 4 adapted to cooperate with a screw-cap 91.

The adapter-bottle cap 101 is secured to the container neck 9 by being provided with a retaining snap ring 93 cooperating with the screw-cap 93. To secure imperviousness, a teflon seal ring 95 may be provided between the adaptor-bottle cap 101 and the container neck 9.

A way to gather the whole device is to press fit the teflon spacer ring 95 in the swivel seal bushing 97, then to install the retaining snap ring 95 on the adapter-container cap 93, then to press fit the bottom of the venting tube 49 to the tube 32, then to install the teflon seal ring 95 into the screw-cap 93 and finally to gather said screw-cap 93 on the adapter container cap 93.

Figure 5:
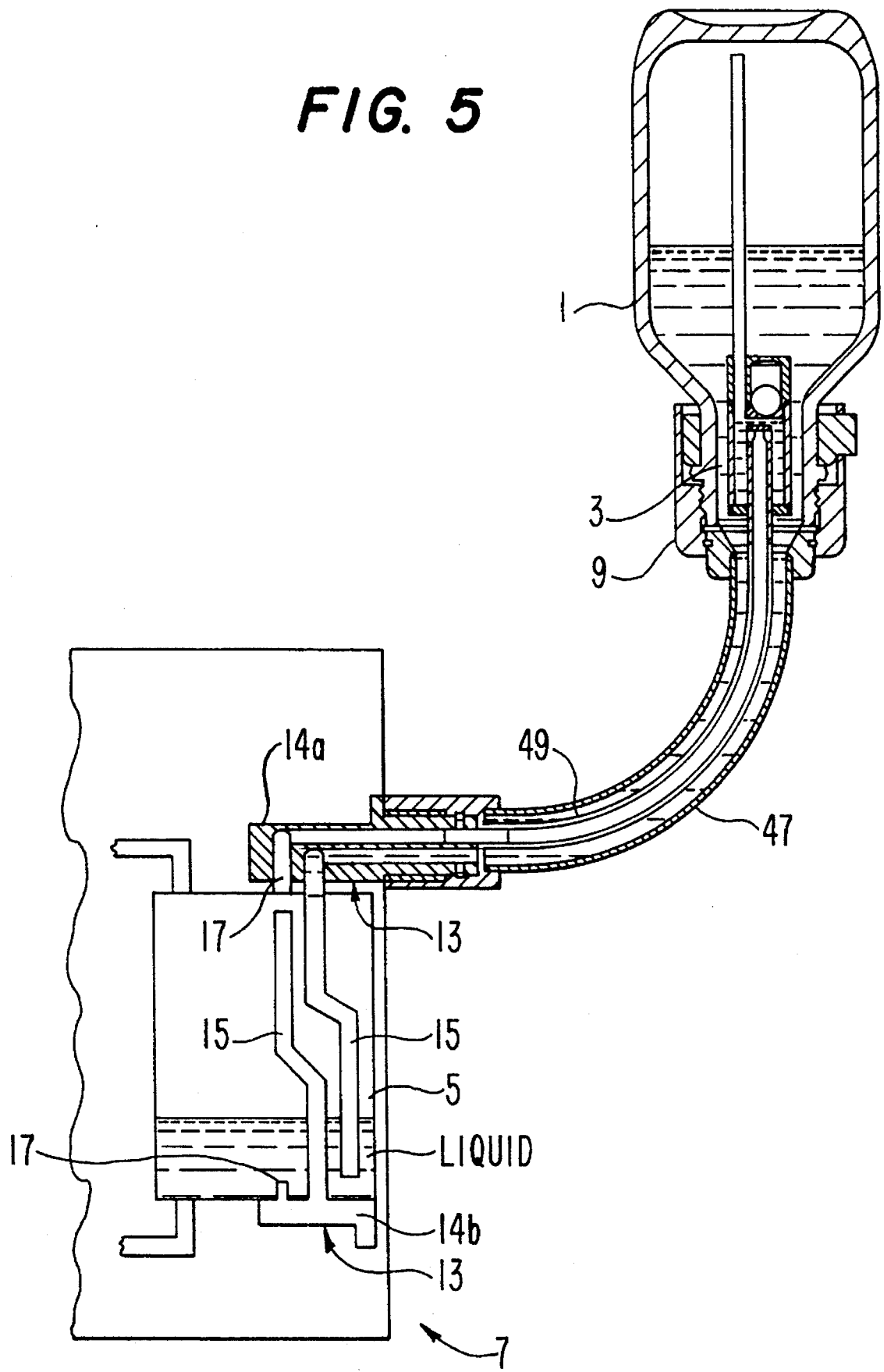
FIG. 5: is a schematic view oa an arrangement according the invention, connected to a second container of an anesthitic vaporizer (only represented in part).

Advantageously, as illustrated in FIGS. 5, the second container defines a reservoir 5 which is part of the anesthetic vaporizer 7. This reservoir 5 is provided with two apertures 13 respectively defining a filling socket 14a and an emptying socket 14b, each socket having one pair of channels that permits a fluid communication between the reservoir 5 and the bottle 3. The pair of channels of the filling socket 14a respectively defines when filling the reservoir 5, a portion of the transfer channel 15 and a portion of the venting channel 17. The pair of channels of the emptying socket 14b respectively defines when emptying the reservoir 5, a portion of the transfer channel 15 and a portion of the venting channel 17.

Advantageously, means for connecting apertures 11 and 13 together may comprise:

a key 43 having opposite ends and an outer longitudinal surface 45 (which surface is preferably cylindrical), said key 43 defining a portion of the transfer channel 15 and a portion of the venting channel 17, said portion of channels 15 and 17 having opposite ends, one end of each channel being provided in one end of the key 43 while the opposite end is provided in the outer longitudinal surface 45 of said key 43;

a rigid curved tube 47 having opposite ends;

fifth connecting means for connecting one end of said rigid curved tube 47 on one end of the key 43 and with the portion of the transfer channel 15 located in the key 43, and sixth connecting means for connecting the opposite end of said rigid curved tube 47 on the neck 9 of the bottle 3 and set the aperture 11 in fluid communication with the portion of the transfer channel located in the rigid curved tube 47;

a venting tube 49 defining a portion of the venting channel 17 and having opposite ends;

seventh connecting means for connecting one end of said venting tube 49 with the portion of the venting channel 17 of the key 43, and eighth connecting means for connecting the opposite end of the venting tube 49 to the second opening 25 of the hollow casing 19;

the portion of the transfer and venting channels 15 and 17 located in the key 43 being positioned on the outer longitudinal surface 45 of said key 43 to align them with any of the corresponding portion of the transfer and venting channels 15 and 17 for filling or emptying of the reservoir 5.

Preferably, the venting tube 49 is co-axially positioned inside the rigid curved tube 47.

Preferably, the gas may consist of air and the liquid may consist of an anesthetic in liquid form.

Advantageously, another preferred embodiment of the invention may consist of an arrangement 51 of the type comprising in combination a device 1 as defined hereinbefore, a first container, especially a bottle 3, and first connecting means adapted to put the first container in fluid communication with a second container, especially the reservoir 5 of an anesthetic vaporizer 7, the first container having one aperture through which fluid matters may flow and the second container having two apertures through which fluid matters may flow, the first connecting means being as defined hereinbefore. Said containers and channels when connected, define a closed system filled with at least one liquid and at least one gas. A first of said channels is essentially a transfer channel for the liquid and a second of said channels is essentially a venting channel for the gas. Each of said channels has opposite ends with one end thereof substantially positioned near a portion of the first container, especially the bottle 3, that is substantially close of the aperture, especially the aperture 11 of the bottle 3, of the first container.

Advantageously, another preferred embodiment of the invention may consist of a method for the transfer by gravity of a liquid from a first container, especially a bottle 3, to a second container, especially the reservoir 5 of an anesthetic vaporizer 7, and vice versa while preventing a "gas-lock", especially "air-lock". Each of said containers have one aperture through which fluids matters may flow. The apertures 11 and 13 are connectable together by first connecting means provided with channels. These containers and channels define a closed system filled with at least one liquid and at least one gas. A first of said channels is essentially a transfer channel 15 for the liquid and a second of said channels is essentially a venting channel 17 for the gas. Each of said channels have opposite ends with one end thereof substantially positioned near a portion of the first container that is close of the aperture of the first container, especially near a portion to the neck of the bottle 3 that is close the aperture 11, the end of the venting channel 17 being provided with a device 1 as defined hereinbefore.

When the apertures 11 and 13 are connected by first connecting means as defined above, and the bottle 3 contains a liquid, such as a liquid anesthetic, to be transferred in the reservoir 5 of the anesthetic vaporizer 7, the bottle 3 is positioned at a point higher than the reservoir 5 to pass the liquid through the aperture 11 of the bottle 3, the transfer channel 15 and the aperture 13 of the reservoir 5 to fill this reservoir 5 while the liquid eventually contained in the third channel 29 is transferred in the reservoir 21 of the hollow casing 19 and the gas contained in the reservoir 5 is vented from the reservoir 5 and transferred in the bottle 3 through the aperture 13 of the reservoir 5, the venting channel 17 and the aperture 11 of bottle 3 via the second opening 25 of the hollow casing 19, the reservoir 21, the first opening 23 of the device and the third channel 29.

When the apertures 11 and 13 are connected by first connecting means as defined above, and said reservoir 5 contains a liquid, especially a liquid anesthetic, to be transferred in the bottle 3, this bottle 3 is positioned at a point lower than the reservoir 5 to make the liquid to pass through the aperture 13 of the reservoir 5, the transfer channel 15, the aperture 11 of the bottle 3 while the gas contained in the bottle 3 is vented from the bottle 3 and transferred in the reservoir 5 through the aperture 11 of the bottle 3 via the check valve 25, the third opening 27 of the hollow casing 19, the hollow casing 19, the second opening 25 of the hollow casing 19, the venting channel 17 and the aperture 13.

When the device is in a emptying position as on FIG. 3, the liquid flows away from the vaporizer by the rigid curved tube 47 to the bottle 3. Air or other gas can be vented through the check valve 31 by lateral opening 35, then by the third opening 27 and at least by the opening 25, a ball 9 being against the element 41.

Figure 4:
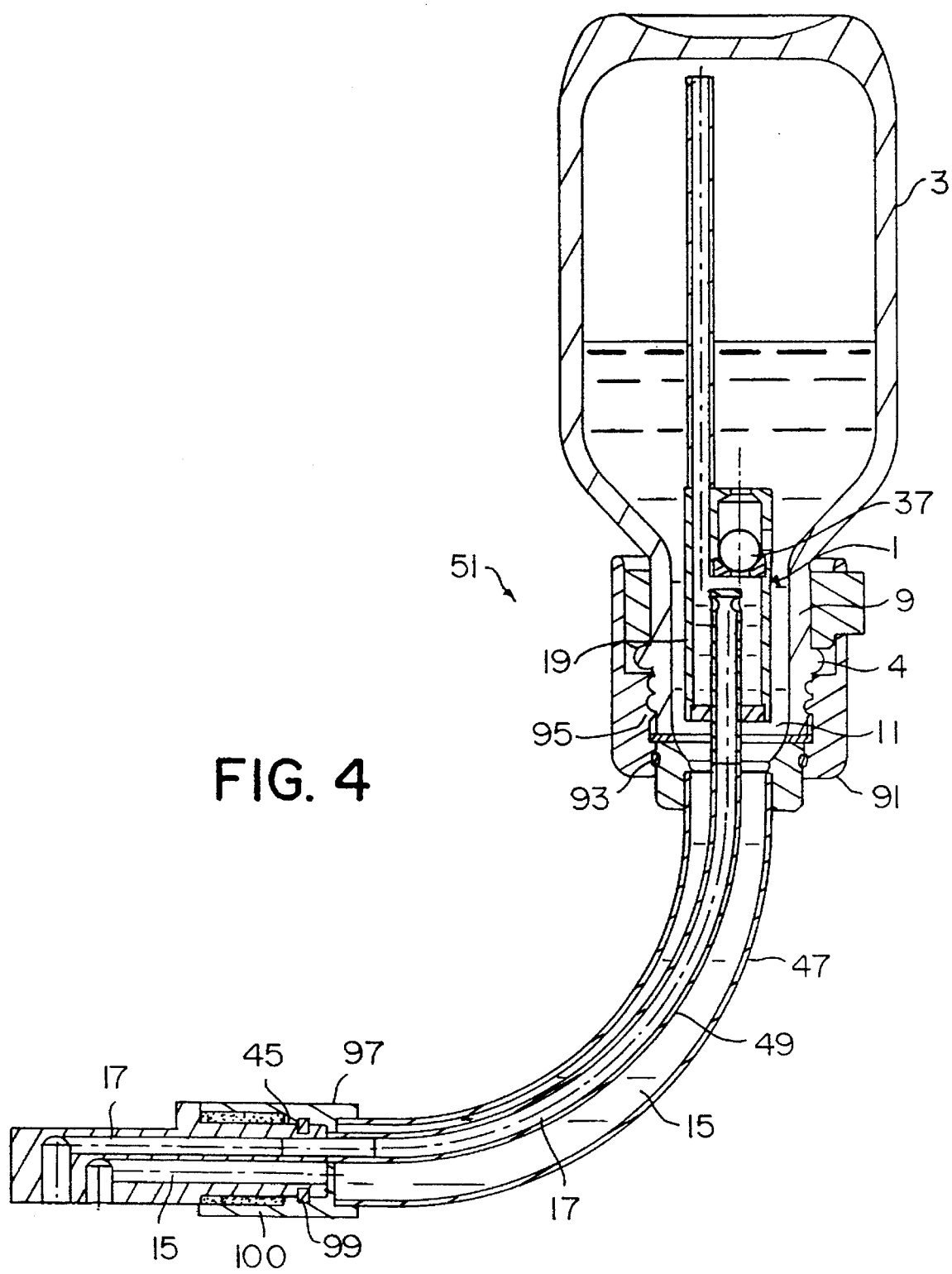
FIG. 4: is a cross-sectional view of an arrangement comprising a device according to the invention for supplying and withdrawing liquid in a closed circuit, the check valve of the device being in a position as in FIG. 2.

When the device is turned upside-down to be in a filling position, like shown on FIG. 4, liquid can go through the rigid curved tube 47 to fill the reservoir 5 of he anesthetic vaporizer 7. The ball 37 moves against the seat 39 to obturate the third opening 27. So the air or other gas can refill the container by going through the tube 32 then the tube 49. During the turning over the small quantity of liquid contained in the tube 49 is moved and stocked into the reservoir 21 so the passage of gas in not embarrassed and the "air-lock" phenomena cannot appear.

Obviously the device according to the invention can be used in any type of closed-system and not only for filling and/or emptying an anesthetic vaporizer.

The present invention is not limited to the above description of preferred embodiment and of course also cover all the variation that may appear obvious to a skilled workman.

What is claimed is:

1. A device for preventing a "gas-lock" when a liquid is transferred by gravity from a first container to a second container and vice versa, each of the containers having at least one aperture through which fluid matters may flow, these apertures being connectable together by first connecting means provided with channels, said containers and channels when connected, defining a closed system filled with at least one liquid and at least one gas, a first of said channels defining essentially a transfer channel for the liquid and a second of said channels defining essentially a venting channel for the gas, each of said channels having opposite ends with one end thereof substantially positioned near a portion of the first container that is substantially close of the aperture of the first container, wherein said device comprises:

a hollow casing defining a reservoir of given capacity and having a lower portion and a set of three openings, said openings consisting of:
  a first opening substantially positioned at the lower portion of the hollow casing;
  a second opening positioned near a bottom of the reservoir;
  a third opening substantially positioned at the lower portion of the hollow casing;
second connecting means adapted for connecting a corresponding end of the second channel to the second opening;
a third channel having opposite ends, one end of said third channel being adapted to be positioned near a portion of the first container that is opposite to its aperture;
third connecting means for connecting the end of the third channel that is opposite the one adapted to be positioned near a portion of the first container that is opposite to its aperture, to the first opening;
a gravity actuated means for selectively enabling the liquid contained in the first container to pass through said third opening;
the capacity of the reservoir being sufficient to collect when the first container is oriented such that the third channel is positioned above the reservoir, all the liquid that may be contained in the third channel and allow inside the hollow casing a free passage for the gas between said first and second openings.

2. A device according to claim 1, wherein the second opening is part of a tube having opposite ends and is at least in part, housed inside the hollow casing, one end of this tube being positioned near the bottom of the hollow casing while the opposite end is adapted to be connected with the corresponding end of the venting channel.

3. A device according to claim 2, wherein the gravity actuated means check valve comprises:
  a sleeve having opposite ends and at least one lateral opening;
  means for connecting one end of said sleeve to the hollow casing and aligning it with the third opening;
  a member housed inside said sleeve;
  a seat for the member, said seat being positioned between the third opening and the lateral opening of the sleeve;
  retaining means for retaining the member inside the sleeve;
said member being movable by gravity between two distinct positions, that is a first position where it is seated against the seat to substantially seal the third opening, and a second position where it contacts said retaining means and allow a fluid communication between the lateral opening of the sleeve and the inside of the casing through said third opening.

4. An arrangement of the type comprising in combination a device as defined in claim 3, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

5. A device according to claim 3, wherein the second container is part of an anesthetic vaporizer provided with two apertures respectively defining a filling socket and an emptying socket, each aperture having one pair of channels communicating with said second container, the pair of channels of the filling socket respectively defining when filling the second container, transfer and venting channels and the pair of channels of the emptying socket respectively defining when emptying the second container, transfer and venting channels; the first container is a bottle having an aperture and a neck, and means for connecting the aperture of the bottle with one aperture of the second container comprise:
  a key having opposite ends and an outer longitudinal surface, said key being provided with a transfer channel and a venting channel having opposite ends, one end of each channel being provided in one end of the key while the opposite end is provided in the outer longitudinal surface of said key;
  a rigid curved tube having opposite ends;
  a fifth connecting means for pivotally connecting one end of said rigid curved tube on one end of the key and with the transfer channel of the key, and a sixth connecting means for connecting the opposite end of said rigid curved tube on the neck of the bottle and set the aperture of the first container in fluid communication with the rigid curved tube;
  a venting tube having opposite ends and defining a venting channel;
  a seventh connecting means for connecting one end of said venting tube on the venting channel of the key, and a eighth connecting means for connecting the opposite end of the venting tube to the second opening of the hollow casing;

one of the ends of the transfer and venting channels of the key being positioned on the outer longitudinal surface of said key to be aligned with any of the corresponding transfer and venting channels for filling or emptying of the second container by mere rotation of the key in the aperture around a longitudinal axis of the key.

6. A device according to claim 5, wherein the venting tube is co-axially positioned inside the rigid curved tube.

7. A device according to claim 6, wherein the member in the sleeve consists of a sphere.

8. A device according to claim 7, wherein the gas consists of air.

9. An arrangement of the type comprising in combination a device as defined in claim 5, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

10. An arrangement of the type comprising in combination a device as defined in claim 2, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

11. A device according to claim 1, wherein the gravity actuated means is a gravity actuated check valve comprising:

a sleeve having opposite ends and at least one lateral opening;

means for connecting one end of said sleeve to the hollow casing and aligning it with the third opening;

a member housed inside said sleeve;

a seat for the member, said seat being positioned between the third opening and the lateral opening of the sleeve;

retaining means for retaining the member inside the sleeve; said member being movable by gravity between two distinct positions, that is a first position where it is seated against the seat to substantially seal the third opening, and a second position where it contacts said retaining means and allow a fluid communication between the lateral opening of the sleeve and the inside of the casing through said third opening.

12. An arrangement of the type comprising in combination a device as defined in claim 11, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

13. A device according to claim 1, wherein the second container is part of an anesthetic vaporizer provided with two apertures respectively defining a filling socket and an emptying socket, each aperture having one pair of channels communicating with said second container, the pair of channels of the filling socket respectively defining when filling the second container, transfer and venting channels and the pair of channels of the emptying socket respectively defining when emptying the second container, transfer and venting channels; the first container is a bottle having an aperture and a neck, and means for connecting the aperture of the bottle with one of the apertures of the second containers comprise:

a key having opposite ends and an outer longitudinal surface, said key being provided with a transfer channel and a venting channel having opposite ends, one end of each channel being provided in one end of the key while the opposite end is provided in the outer longitudinal surface of said key;

a rigid curved tube having opposite ends;

fifth connecting means for connecting one end of said rigid curved tube on one end of the key and with the transfer channel of the key, and sixth connecting means for connecting the opposite end of said rigid curved tube on the neck of the bottle and set the aperture of the first container in fluid communication with the rigid curved tube;

a venting tube having opposite ends and defining a venting channel;

seventh connecting means for connecting one end of said venting tube on the venting channel of the key, and eighth connecting means for connecting the opposite end of the venting tube to the second opening of the hollow casing;

one of the ends of the transfer and venting channels of the key being positioned on the outer longitudinal surface of said key to be aligned with any of the corresponding transfer and venting channels of the filling or emptying socket.

14. A device according to claim 13, wherein the venting tube is co-axially positioned inside the rigid curved tube and wherein the end of the rigid curved tube connected on the corresponding end of the key, is co-axially pivotable on the outer longitudinal surface of the key.

15. An arrangement of the type comprising in combination a device as defined in claim 14, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

16. An arrangement of the type comprising in combination a device as defined in claim 13, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

17. A device according to claim 1, wherein the member in the sleeve consists of a sphere.

18. A device according to claim 1, wherein the gas consists of air.

19. An arrangement of the type comprising in combination a device as defined in claim 1, a first container and first connecting means adapted to put the first container in fluid communication with a second container, each of the containers having at least one aperture through which fluid matters may flow, the first connecting means being provided with channels connecting at least one aperture of the first container with at least one aperture of the second container, said containers and channels when connected, defining a closed system filled with at least one liquid and at least one gas, a first of said channels defining essentially a transfer channel for the liquid and a second of said channels essentially a venting channel for the gas, each of said channels having opposite ends with one end thereof substantially positioned near a portion of the first container that is substantially close of the aperture of the first container.

20. A method for the transfer by gravity of a liquid from a first container to a second container and vice versa while preventing a "gas-lock", each of said containers having at least one aperture through which fluids matters may flow, these apertures being connectable together by first connecting means provided with channels, said containers and channels defining a closed system filled with at least one liquid and at least one gas, a first of said channels defining essentially a transfer channel for the liquid and a second of said channels defining essentially a venting channel for the gas, each of said channels having opposite ends with one end thereof substantially positioned near a portion of the first container that is close of the aperture of the first container, the end of the venting channel being provided with a device comprising:

a hollow casing defining a reservoir of given capacity and having a lower portion and a set of three openings, said openings consisting of:

a first opening substantially positioned at the lower portion of the hollow casing;

a second opening positioned near a bottom of the reservoir;

a third opening substantially positioned at the lower portion of the hollow casing, second connecting means adapted for connecting a corresponding end of the second channel with said second opening;

a third channel having opposite ends, one end of said third channel being adapted to be positioned near a portion of the first container that is opposite to the aperture of the first container;

third connecting means for connecting the end of the third channel that is opposite the one adapted to be positioned near the portion of the first container that is opposite the aperture of the first container, to the first opening;

a gravity actuated means for selectively enabling the liquid contained in the first container to pass through said third opening;

the capacity of the reservoir being sufficient to collect when the first container is oriented such that the third channel is positioned above the reservoir, all the liquid that may fill the third channel and allow inside the hollow casing a free passage for gas between said first and second openings; wherein when the first and the second containers are connected by first connecting means for filling purposes and said first container contains a liquid to be transferred in the second container, the first container is moved from a position located at a point lower than the second container to a position located at a point higher than the second container to pass the liquid through the aperture of the first container, the transfer channel and the aperture of the second container to fill this second container while the liquid eventually contained in the third channel is transferred into the reservoir of the device and the gas contained in the second container is vented from the second container and transferred in the first reservoir through the aperture of the second container, the venting channel and the aperture of the first container via the second opening of the device, the hollow casing, the first opening of the device and the third channel;

when the first and the second container are connected by first connecting means for emptying purposes and said second container contains a liquid to be transferred in the first container, the first container is moved from a position located at a point higher than the second container to a position located at a point lower than the second container to pass the liquid through the aperture of the second container, the transfer channel, the aperture of the first container while the gas contained in the first container is vented from the first container and transferred in the second container through the aperture of the first container, the gravity actuated means, the third opening of the hollow casing, the hollow casing, the second opening of the hollow casing, the venting channel and the aperture of the second channel.

21. A method for the transfer by gravity of a liquid from a first container to a second container and vice versa, while preventing an "air-lock", each of said containers having at least one aperture through which fluids matters may flow, these apertures being connectable together by first connecting means provided with channels, said containers and channels when connected, defining a closed system filled with at least one liquid and at least air, a first of said channels defining essentially a transfer channel for the liquid and a second of said channels defining essentially a venting channel for air, each of said channels having opposite ends with one end thereof substantially positioned near a portion of the first container that is close of the aperture of the first container, the end of the venting channel being provided with a device comprising:

a hollow casing defining a reservoir of given capacity and having a lower portion and a set of three openings, said openings consisting of:
 a first opening substantially positioned at the lower portion of the hollow casing;
 a second opening positioned near a bottom of the reservoir;
 a third opening substantially positioned at the lower portion of the hollow casing;
second connecting means adapted for connecting a corresponding end of the second channel with said second opening;
a third channel having opposite ends, one end of said third channel being adapted to be positioned near a portion of the first container that is opposite, to the aperture of the first container;
third connecting means for connecting the end of the third channel that is opposite the one adapted to be positioned near the portion of the first container that is opposite the aperture of the first container, to the first opening;
a gravity actuated check valve;
fourth connecting means for connecting the gravity actuated check valve with respect to the third opening and for selectively enabling the liquid contained in the first container to pass through said third opening;
the capacity of the reservoir, being sufficient to collect when, the first container is oriented such that the third channel is above the reservoir, all the liquid that may fill the third channel and allow inside the hollow casing a free passage for air between said first and second openings; wherein when the first and the second containers are connected by first connecting means for filling purposes and said first container contains a liquid to be transferred in the second container, the first container is moved from a position located at a point lower than the second container to a position located at a point higher than the second container to pass the liquid through the aperture of the first container, the transfer channel and the aperture of the second container to fill this second container while the liquid eventually contained in the third channel is transferred into the reservoir of the device and the gas contained in the second container is vented from the second container and transferred in the first reservoir through the aperture of the second container, the venting channel, the aperture of the first container, the second opening of the device, the hollow casing, the first opening of the device and the third channel;

when the first and the second container are connected by first connecting means for emptying purposes and said second container contains a liquid to be transferred in the first container, the first container is moved from a position located at a point higher than the second container to a position located at a point lower than the second container to pass the liquid through the aperture of the second container, the transfer channel, the aperture of the first container while the gas contained in the first container is vented from the first container and transferred in the second container through the aperture of the first container, the gravity actuated check valve, the third opening of the hollow casing, the hollow casing, the second opening of the hollow casing, the venting channel and the aperture of the second channel.

22. A device according to claim 21, wherein the second container is part of an anesthetic vaporizer provided with two apertures respectively defining a filling socket and an emptying socket, each aperture having one pair of channels communicating with said second container, the pair of channels of the filling socket respectively defining when filling the second container, transfer and venting channels and the pair of channels of the emptying socket respectively defining when emptying the second container, transfer and venting channels; the first container is a bottle having an aperture and a neck, and means for connecting the aperture of the bottle with one aperture of the second container comprise:

a key having opposite ends and an outer longitudinal surface, said key being provided with a transfer channel and a venting channel having opposite ends, one end of each channel being provided in one end of the key while the opposite end is provided in the outer longitudinal surface of said key;

a rigid curved tube having opposite ends;

a fifth connecting means for pivotally connecting one end of said rigid curved tube on one end of the key and with the transfer channel of the key, and a sixth connecting means for connecting the opposite end of said rigid curved tube on the neck of the bottle and set the aperture of the first container in fluid communication with the rigid curved tube;

a venting tube having opposite ends and defining a venting channel;

a seventh connecting means for connecting one end of said venting tube on the venting channel of the key, and a eighth connecting means for connecting the opposite end of the venting tube to the second opening of the hollow casing;

one of ends of the transfer and venting channels of the key being positioned on the outer longitudinal surface of said key to be aligned with any of the corresponding transfer and venting channels for filling or emptying of the second container by mere rotation of the key in the aperture around a longitudinal axis of the key.

23. A device according to claim 22, wherein the venting tube is co-axially positioned inside the rigid curved tube.

24. A device according to claim 23, wherein the member in the sleeve consists of a sphere.

* * * * *